United States Patent
Shvets et al.

(10) Patent No.: US 11,415,509 B2
(45) Date of Patent: Aug. 16, 2022

(54) SYSTEM AND METHOD FOR REFLECTIVE SPECTROSCOPY OF A CELL MEMBRANE USING A FIBER WITH A PLASMONIC METASURFACE

(71) Applicant: CORNELL UNIVERSITY, Ithaca, NY (US)

(72) Inventors: Gennady Shvets, Ithaca, NY (US); Shourya Dutta Gupta, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 466 days.

(21) Appl. No.: 16/611,912

(22) PCT Filed: May 8, 2018

(86) PCT No.: PCT/US2018/031599
§ 371 (c)(1),
(2) Date: Nov. 8, 2019

(87) PCT Pub. No.: WO2018/208774
PCT Pub. Date: Nov. 15, 2018

(65) Prior Publication Data
US 2021/0080387 A1    Mar. 18, 2021

Related U.S. Application Data

(60) Provisional application No. 62/502,813, filed on May 8, 2017.

(51) Int. Cl.
*G01J 3/44* (2006.01)
*G01N 21/3563* (2014.01)
*G01N 21/552* (2014.01)

(52) U.S. Cl.
CPC ........ *G01N 21/3563* (2013.01); *G01N 21/554* (2013.01)

(58) Field of Classification Search
CPC ................ G01N 21/65; G01N 21/658; G01N 2021/656; G01J 3/44; G01J 3/02
(Continued)

(56) References Cited

U.S. PATENT DOCUMENTS 8,761,865 B2    6/2014  Babchenko
8,921,789 B2    12/2014 Pryce et al.
(Continued)

OTHER PUBLICATIONS

Morgan, M. S. C., et al., Light Reflectance Spectroscopy to Detect Positive Surgical Margins on Prostate Cancer Specimens. The Journal of Urology 195, 479-484 (2016).
(Continued)

*Primary Examiner* — Md M Rahman
(74) *Attorney, Agent, or Firm* — Barnes & Thornburg LLP

(57) ABSTRACT

An integrated device for the detection of cancerous tissue including an optical fiber configured to receive at a first end modulated infrared light and to conduct the modulated infrared light from the first end to a second end; and a plasmonic metasurface, disposed on the second end of the optical fiber, configured to localize evanescent infrared light to sub-100 nanometer distances from the plasmonic metasurface of the optical fiber such that the localized evanescent infrared light penetrates only the membrane portion of a cell held against the second end, wherein the second end is configured to receive reflected light reflected from the membrane portion the cell, the reflected light including spectroscopic information indicative of whether the cell is noncancerous or cancerous.

15 Claims, 10 Drawing Sheets

(58) Field of Classification Search
USPC .......................................................... 356/301
See application file for complete search history.

(56) References Cited

U.S. PATENT DOCUMENTS

| 9,844,334 B2* | 12/2017 | Stewart ............ A61B 17/00234 |
| 2016/0341859 A1 | 11/2016 | Shvets et al. |
| 2016/0370568 A1 | 12/2016 | Toussaint et al. |

OTHER PUBLICATIONS

Bassan, P., et al., Resonant Mie scattering in infrared spectroscopy of biological materials—understanding the dispersion artefact. Analyst 134, 1586-1593 (2009).

Diem, M., et al., Applications of Infrared and Raman Microspectroscopy of Cells and Tissue in Medical Diagnostics: Present Status and Future Promises. Spectroscopy: An International Journal 27, 463-496 (2012).

Wong, P., et al., Infrared spectroscopy of exfoliated human cervical cells: evidence of extensive structural changes during carcinogenesis. Proceedings of the National Academy of Sciences 88 (24), 10988-10992 (1991).

Cohenford, M. A. et al., Cytologically normal cells from neoplastic cervical samples display extensive structural abnormalities on IR spectroscopy: implications for tumor biology. Proceedings of the National Academy of Sciences 95 (26), 15327-15332 (1998).

Argov, S., et al., Diagnostic potential of Fourier-transform infrared microspectroscopy and advanced computational methods in colon cancer patients. Journal of biomedical optics 7 (2), 248-254 (2002).

Tfayli, A., et al., Discriminating nevus and melanoma on paraffin embedded skin biopsies using FTIR microspectroscopy. Biochimica et Biophysica Acta (BBA)—General Subjects 1724(3), 262-269 (2005).

Mordechai, S., et al., Possible common biomarkers from FTIR microspectroscopy of cervical cancer and melanoma. Journal of microscopy 215 (1), 86-91 (2004).

Petibois, C. et al., Chemical mapping of tumor progression by FT-IR imaging: towards molecular histopathology. Trends in biotechnology 24 (10), 455-462 (2006).

Tobin, M. J., et al., Infrared microscopy of epithelial cancer cells in whole tissues and in tissue culture, using synchrotron radiation. Faraday discussions 126, 27-39 (2004).

Walsh, M. J., et al., IR microspectroscopy: potential applications in cervical cancer screening. Cancer letters 246 (1), 1-11 (2007).

Martin, F. L., et al., Distinguishing cell types or populations based on the computational analysis of their infrared spectra. Nature Protocols 5, 1748-1760 (2010).

Mostaco-Guidolin, L. B. et al,. Application of FTIR spectroscopy for identification of blood and leukemia biomarkers: A review over the past 15 years. Applied Spectroscopy Reviews 46 (5), 388-404 (2011).

Derenne, A., et al., The FTIR spectrum of prostate cancer cells allows the classification of anticancer drugs according to their mode of action. Analyst 136, 1134-1141 (2011).

Kastl, L., et al., Potential of mid IR spectroscopy in the rapid label free identification of skin malignancies. Proc. of SPIE 9703, 970307 (2016).

Hollingsworth, M. A. et al., Mucins in cancer: protection and control of the cell surface. Nature Reviews Cancer 4, 45-60 (2004).

Cavallaro, U. et al., Cell adhesion and signalling by cadherins and Ig-CAMs in cancer. Nature Reviews Cancer 4, 118 (2004).

Jiang, W., et al., Elucidation of Functional Groups on Gram-Positive and Gram-Negative Bacterial Surfaces Using Infrared Spectroscopy. Langmuir 20, 11433-11442 (2004).

Steyer, J. A. et al., Nature Reviews | Molecular Cell Biology 2, 268 (2001).

Ataka, K. et al., Biochemical applications of surface-enhanced infrared absorption spectroscopy. Anal Bioanal Chem 388, 47-54 (2007).

Jiang, X., et al., Resolving voltage-dependent structural changes of a membrane photoreceptor by surface-enhanced IR difference spectroscopy. Proc. Natl Acad. Sci. USA 105, 12113-12117 (2008).

Enders, D., et al., Surface Enhanced Infrared Absorption on Au Nanoparticle Films Deposited on SiO2/Si for Optical Biosensing: Detection of the Antibody-Antigen Reaction. Surf. Sci. 600, L305-L308 (2006).

Zaitseva, E., et al., SEIRA Spectroscopy on a Membrane Receptor Monolayer Using Lipoprotein Particles as Carriers. Biophysical Journal 99, 2327-2335 (2010).

Wu, C., et al., Metamaterial-based integrated plasmonic absorber/emitter for solar thermo-photovoltaic systems. J. Opt. 14, 024005 (2012).

Wu, C., et al., Fano-resonant asymmetric metamaterials for ultrasensitive spectroscopy and identification of molecular monolayers. Nature Mater. 11, 69-75 (2012).

Cubukcu, E., et al., Split ring resonator sensors for infrared detection of single molecular monolayers. Appl. Phys. Lett. 95, 043113 (2009).

Hocde, S., et al., Metabolic imaging of tissues by infrared fiber-optic spectroscopy: An efficient tool for medical diagnosis. J. Biomed. Opt. 9, 404 (2004).

Lucas, P., et al., Evaluation of toxic agent effects on lung cells by fiber evanescent wave spectroscopy (FEWS). Appl. Spectrosc. 59, 1 (2005).

Lucas, P., et al., Advances in chalcogenide fiber evanescent-wave biochemical sensing. Anal. Biochem. 351, 1 (2006).

Wilhelm, A. A., et al., Biocompatibility of Te—As—Se glass fibers for cell-based biooptic infrared sensors. J. Mater. Res. 22, 1098 (2007).

Mcintosh, L. M., et al., Towards Non-Invasive Screening of Skin Lesions by Near-Infrared Spectroscopy. J. Invest. Dermatol. 116, 175 (2001).

Izzard, C. S. et al., Cell-To-Substrate Contacts in Living Fibroblasts: an Interference Reflexion Study With an Evaluation of the Technique. J. Cell. Sc. 21, 129 (1976).

Seddon, A. B., Mid-infrared (IR)—A hot topic: The potential for using mid-IR light for non-invasive early detection of skin cancer in vivo. Phys. Status Solidi B 250, 1020 (2013).

Parnell, H., et al., Ge—Sb—Se glass fiber-optics for in-vivo mid-infrared optical biopsy. Proc. of SPIE 9703, 970309 (2016).

Hammody, Z., et al., Distinction of malignant melanoma and epidermis using IR micro-spectroscopy and statistical methods. Analyst 133, 372-378 (2008).

Ly, E., et al., Differential diagnosis of cutaneous carcinomas by infrared spectral micro-imaging combined with pattern recognition. Analyst 134, 1208 (2009).

Mostac,o-Guidolin, L. B., et al., Fourier transform infrared spectroscopy of skin cancer cells and tissues. Appl. Spectros. 44, 438 (2009).

Finch, D. S., et al., Biocompatibility of atomic layer-deposited alumina thin films. Journal of Biomedical Research A 87, 100 (2008).

Montemor, M. F., Functional and smart coatings for corrosion protection: A review of recent advances. Surface and Coatings Technology 258, 17 (2014).

Chou, S. Y., et al., Nanoimprint lithography. J. Vac. Sci. Technol. B 14, 4129 (1996).

Principe, et al., Meta-tips for lab-on-fiber optrodes, In: Sixth European Workshop on Optical Fibre Sensors, International Society for Optics and Photonics, May 30, 2016, vol. 9916, pp. 1-4; Abstract provided 3 pages.

Limaj, et al., Infrared Plasmonic Biosensor for Real-Time and Label-Free Monitoring of Lipid membranes, Nano letters, Jan. 13, 2016, vol. 16, No. 2, pp. 1502-1508; Abstract provided 10 pages.

International Search Report and Written Opinion for International Application PCT/US2018/031599 dated Sep. 17, 2018, 10 pages.

\* cited by examiner

SYSTEM AND METHOD FOR REFLECTIVE SPECTROSCOPY OF A CELL MEMBRANE USING A FIBER WITH A PLASMONIC METASURFACE

CROSS REFERENCE

This application is a U.S. National Phase filing of International Application No. PCT/US18/31599 filed May 8, 2018, which itself claims priority to U.S. Provisional Patent Application Ser. No. 62/502,813, filed on May 9, 2017, and entitled "Optical Tool, Methods, and Applications," the contents of each of which are hereby incorporated by reference in its entirety.

FIELD OF INVENTION

This application generally relates to a system and method for analyzing a cell membrane using reflective spectroscopy with a fiber having a plasmonic metasurface.

BACKGROUND

One of the most challenging and important decisions faced by an oncologist is to determine what fraction of a neoplasm-containing tissue needs to be surgically removed. The decision is affected by many factors, such as whether the neoplasm is benign or malignant, and the consequences of removing too much tissue. The consequences of this decision to the patient can be most dramatic. They can affect his/her future quality of life, and even the very survival of the patient. Removing insufficient amount of the tissue affected by malignant neoplasia (positive surgical margin, or PSM) may result in cancer recurrence and will adversely affect the course of post-operative therapy. On the other hand, removing excessive amount of the tissue can result in fundamental reduction of the quality of patients' lives. In the case of surgically treated prostate cancer, this may include losses of continence and/or erectile function. Most of the present approaches involve detecting the margins post-operatively during the pathological analysis stage. That precludes making intraoperative decisions that determine both oncological outcomes and subsequent quality-of-life issues.

Recently, there has been an increase in interest in optical detection techniques that can be carried out in vivo and do not require a biopsy. For example, light reflectance spectroscopy (LRS) was used to discriminate between normal and cancerous cells based on their morphological differences. Another highly promising emerging technique is infrared spectroscopic cytology based on the quantification of vibrational fingerprints of cell's constituent molecules (for example, proteins, lipids, phospholipids, etc.).

The biochemical cell's fingerprint associated with the mid-infrared part of the electromagnetic spectrum which overlaps with molecular vibrations ($\omega V = 900-1,800$ cm$^{-1}$) provides a representation of the cellular structure/function based on chemical bond vibrations and provides an excellent (potentially clinical) tool for distinguishing between different cell types and populations. Infrared (IR) spectroscopy has been used in a variety of cell-characterization applications, including the investigations of the effects of anti-cancer drugs on tumor cells.

Guided by the key idea that biochemical information obtainable from IR spectroscopy can be as valuable for medical diagnoses as the morphological information, various spectroscopic modalities have been developed over the years. For example, the IR spectra of skin cells were used for rapid label free identification of skin malignancies.

Despite their promise, most of these approaches have not been applied in an operating room because of the challenge of delivering mid-IR light to tumors inside the body. In fact, most cells' spectral characterizations have been done on the cells that are removed from the body, placed on a substrate, and examined using an infrared microscope coupled to a Fourier Transform Infrared Spectrometer (FTIR). What is clearly preventing the extension of these spectral characterization techniques is the absence of a remote sensing approach.

Furthermore, if the mid-IR spectroscopy is ever going to be implemented intra-operatively, it is absolutely crucial to carry out the spectroscopic characterization of the cells in reflection. But carrying out reflective spectroscopy, with, for example, an unpatterned fiber, faces serious limitations. One limitation is the weakness of the signal. The relatively small reflectivity from the fiber tip is caused by the low refractive index contrast between the fiber and the tissue. The second limitation is more subtle. Specifically, it has been known for some time that the cellular progression from normal to cancerous is accompanied by significant molecular composition changes at the cell's surface, such as significant changes in extracellular proteins and downregulation of cell adhesion molecules. Therefore, there is a need to be able to "see" tens of nanometers deep into the cell, which can only be done using evanescent fields. Optical fibers alone cannot provide such field localization.

SUMMARY

This disclosure is generally related to plasmonic metasurface tipped IR-transparent optical fibers, used to deliver concentrated localized mid-infrared (mid-IR) light directly to the cell membrane and to employ the spectral characteristics of the reflected light to distinguish between normal, pre-cancerous, and cancerous cells that are in contact with the tip of the fiber.

According to an aspect, an integrated device for the detection of cancerous tissue, includes: an optical fiber configured to receive at a first end modulated infrared light and to conduct the modulated infrared light from the first end to a second end; and a plasmonic metasurface, disposed on the second end of the optical fiber, configured to localize evanescent infrared light to sub-100 nanometer distances from the plasmonic metasurface of the optical fiber such that the localized evanescent infrared light penetrates only a membrane portion of a cell held against the second end, wherein the second end is configured to receive reflected light reflected from the membrane portion the cell, the reflected light including spectroscopic information indicative of whether the cell is noncancerous or cancerous.

According to an embodiment, the plasmonic metasurface is configured to enhance the strength of the localized evanescent infrared light.

According to an embodiment, the plasmonic metasurface is configured to enhance the reflection of the evanescent infrared light.

According to an embodiment, the plasmonic metasurface is tuned to resonate at a vibrational band indicative of one of a cellular trans-membrane protein or a phospholipid.

According to an embodiment, the plasmonic metasurface is includes a plurality of antenna pairs arranged in a periodic pattern.

According to an embodiment, each of the antenna pairs comprises a straight antenna and a bent antenna, the bent antenna including a first leg and a second leg, wherein the first leg is arranged substantially parallel to the straight antenna, and the second leg is arranged at one end of the first leg, extending toward the straight antenna and being substantially perpendicular to first leg and the straight antenna.

According to an embodiment, the optical fiber comprises a plurality of cores, each core including, at an end, a respective plasmonic metasurface.

According to another aspect, a method for the detection of cancerous tissue, includes the steps of: providing an optical fiber configured to conduct infrared light from a first end to a second end, and a plasmonic metasurface, disposed on the second end of the optical fiber, configured to localize evanescent infrared light to sub-100 nanometer distances from the plasmonic metasurface; bringing the plasmonic metasurface into contact with a cell; transmitting infrared light through the optical fiber, such that the localized evanescent infrared light penetrates only the membrane portion of the cell; and receiving from the second end reflected light reflected from only a membrane portion of the cell, the reflected light including spectroscopic information indicative of whether the cell is noncancerous or cancerous.

According to an embodiment, the method further includes the step of analyzing the reflected light to determine if the at least one cell is cancerous or noncancerous.

According to an embodiment, the plasmonic metasurface is configured to enhance the strength of the localized evanescent infrared light.

According to an embodiment, the plasmonic metasurface is configured to enhance the reflection of the evanescent infrared light.

According to an embodiment, the plasmonic metasurface is tuned to resonate at a vibrational band indicative of one of a cellular trans-membrane protein or a phospholipid.

According to an embodiment, the plasmonic metasurface is includes a plurality of antenna pairs arranged in a periodic pattern.

According to an embodiment, each of the antenna pairs comprises a straight antenna and a bent antenna, the bent antenna including a first leg and a second leg, wherein the first leg is arranged substantially parallel to the straight antenna, and the second leg is arranged at one end of the first leg, extending toward the straight antenna and being substantially perpendicular to first leg and the straight antenna.

According to an embodiment, the optical fiber comprises a plurality of cores, each core including, at an end, a respective plasmonic metasurface.

These and other aspects of the invention will be apparent from and elucidated with reference to the embodiment(s) described hereinafter

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE INVENTION

Figure 1:
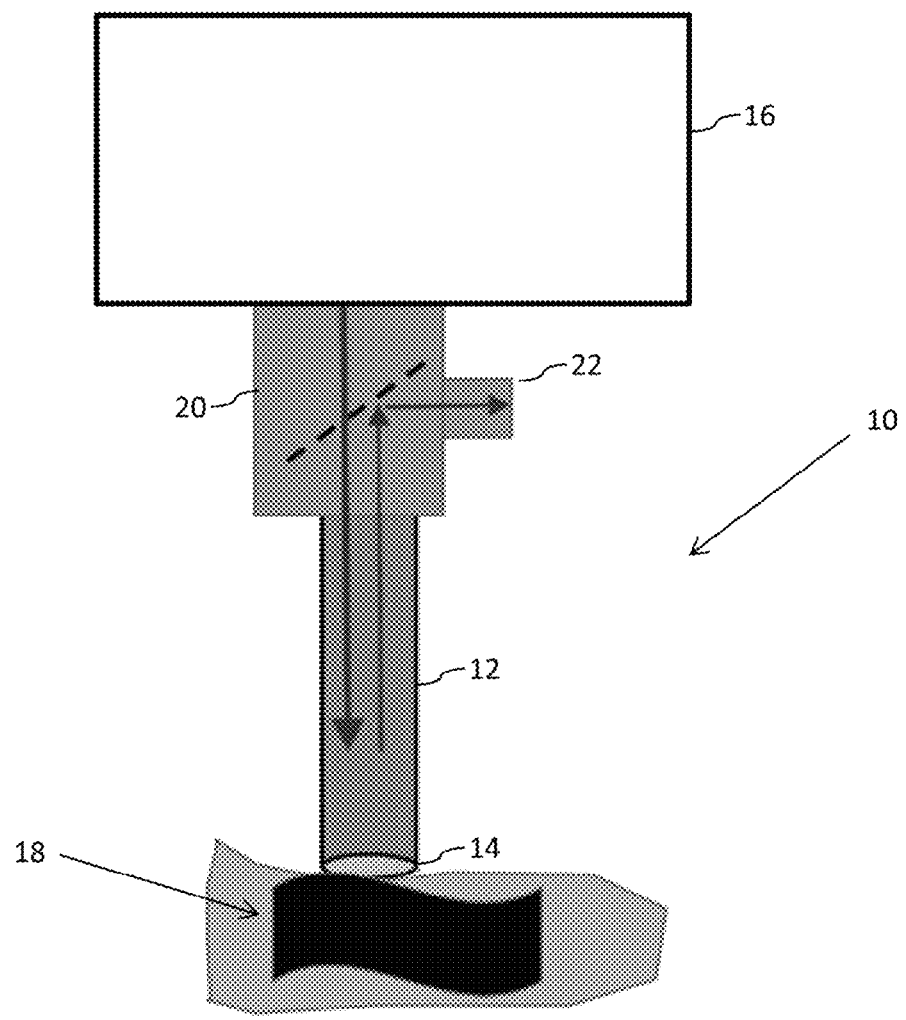
FIG. 1 depicts a block diagram of an integrated device for reflective spectroscopy, according to an embodiment.

There is shown in FIG. 1, a block diagram of an integrated device 10 for detection of cancerous tissue, comprising an IR transparent fiber 12 including, at its tip, a plasmonic metasurface 14. The fiber 12 is operatively connected to receive infrared light from a spectrometer 16. The fiber 12, conducting the IR light to the tip, receives reflection spectra of incoherent light incident onto the plasmonic metasurface 14 through the fiber 12, which is back-propagated into the spectrometer 16 through the fiber 12. At a high level, the integrated device 10 forms a probe that may be brought into intimate contact with a neoplasm (the tissue under test 18) that must be diagnosed or surgically removed. Operating as metasurface-enhanced infrared reflection spectroscopy, the integrated device 10 may thus be used to distinguish between cancerous, precancerous, and noncancerous cells using vibrational fingerprinting.

As will be described in detail below, in order to penetrate, and thus diagnose, only the membrane of the cells comprising the tissue under test, the plasmonic metasurface 14 is configured to provide strong light concentration and localization in the evanescent region and improved reflectivity, as compared to an unpatterned fiber.

As shown in FIG. 1, the fiber 12 may be operatively connected to spectrometer 16 via fiber coupler 20 (although any other method for operatively connecting a spectrometer 16 to fiber 12 may be used). Further, spectrometer 16 may be any type spectrometer sufficient for preparing and transmitting modulated mid-IR light to fiber 12. In an example, spectrometer 16 may be a Fourier Transform InfraRed (FTIR) spectrometer. The reflected IR light, back-propagated through fiber 12, may be receive at spectrometer 16, or any other device, for analysis. In an embodiment, where multiple fiber cores are used (as will be described in detail below), a focal plane array 22 may be employed to analyze the individual signals from each core in parallel.

Figure 2:
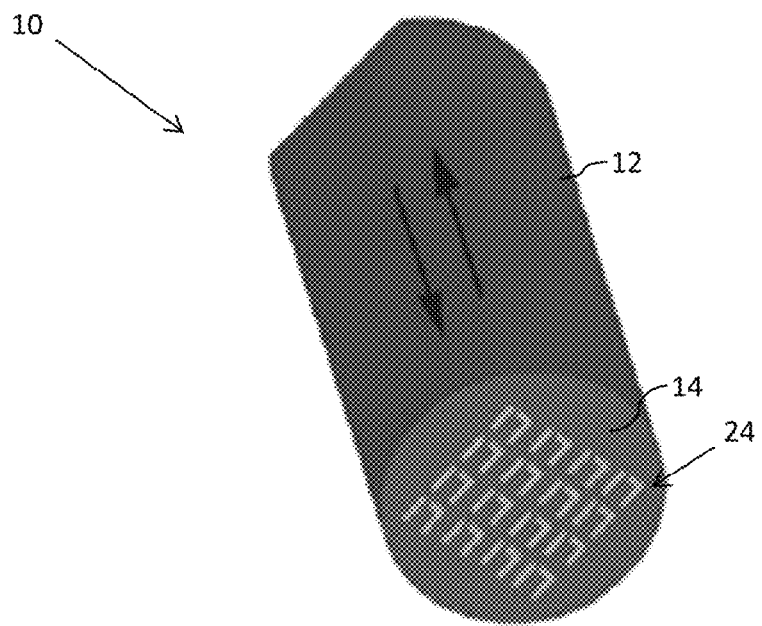
FIG. 2 is a perspective view of a fiber with a plasmonic metasurface, according to an embodiment.

Turning to FIG. 2, there is shown a perspective view of a single-core fiber 12 with plasmonic metasurface 14 disposed on the tip of fiber 12. Fiber 12 may be formed of any material suitable for receiving and transmitting mid-range IR light along its length. Mid-range IR light is used because the cell's fingerprint are associated with the mid-infrared part of the electromagnetic spectrum, which overlaps with molecular vibrations in the range $\omega_v$=900-1800 cm$^{-1}$ providing a representation of the cellular structure and function based on chemical bond vibrations. In an example, fiber 12 may have a chalcogenide core.

Figure 3:
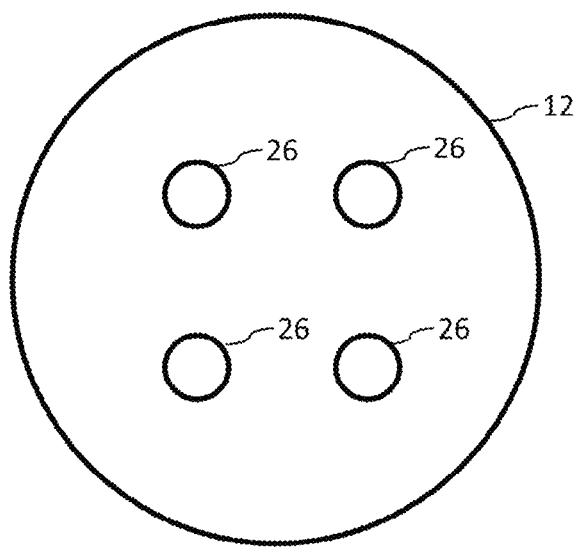
FIG. 3 is a cross section of a multi-core fiber, according to an embodiment.

In an example, and as shown in FIG. 3, fiber 12 may comprise a multi-core fiber. FIG. 3 depicts four cores bundled within fiber 12. In another example, the IR fiber 12 may be formed of 1 mm diameter fiber that carries a ten-by-ten array of chalcogenide cores 26 (any number of cores may be used), each core being tipped with a plasmonic metasurface 14, resulting in 100 spectra of reflected to be analyzed. The multi-core geometry is beneficial because it enables simultaneous collection of spectral signatures from multiple locations on the fiber. Returning to FIG. 2, the plasmonic metasurface may be comprised of periodic patterns of non-trivial metal shapes (e.g., antennas, split rings, etc.) exhibiting tunable infrared resonances that are determined by the shares and sizes of the constituent particles. The resonant frequency of the plasmonic metasurface 14 may be tuned to coincide with important vibrational bands used for identifying the nature and the expression degree of cellular trans-member proteins and phospholipids (e.g., symmetric phosphate, glycogen, and amides' vibration). Further, as described above, the plasmonic metasurface 14 is configured to provide strong light concentration and localization in the evanescent region and improved reflectivity, as compared to an unpatterned fiber.

Figure 4:
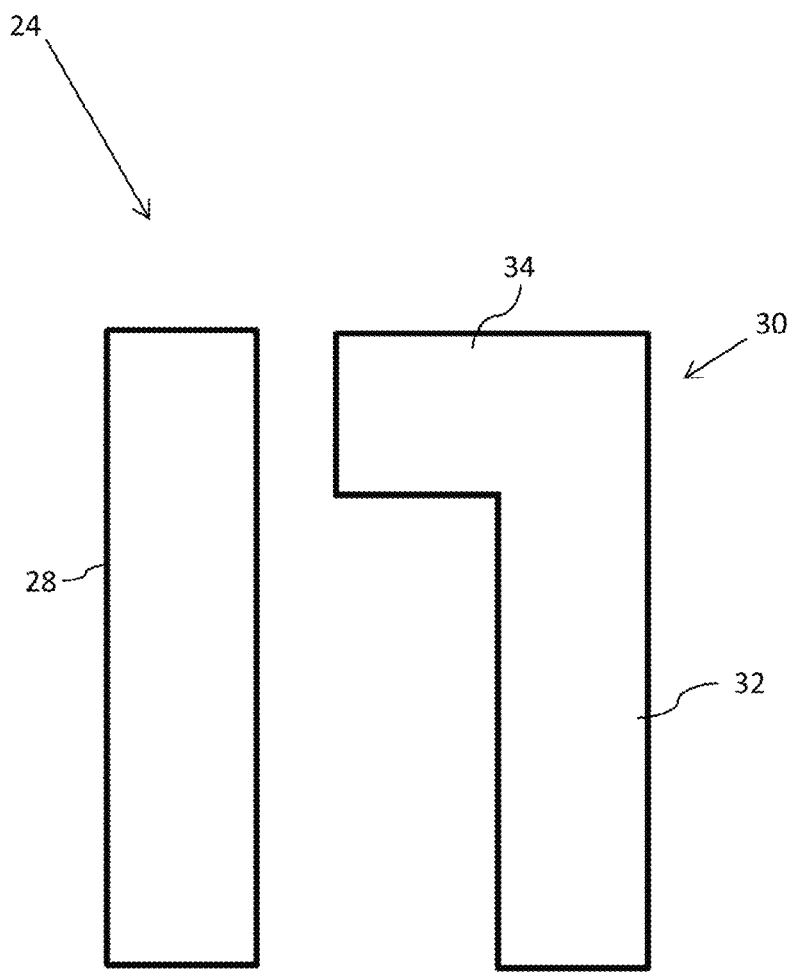
FIG. 4 is a block diagram of an antenna pair, according to an embodiment.

The periodic patterns may, for example, be comprised of a plurality antenna pairs. One such antenna pair is shown in FIG. 4. The antenna pair 24 may comprise a straight antenna 28 and a bent antenna 30. The bent antenna may comprise two legs, including first leg 32 and a second leg 34. The second leg 34 may be substantially perpendicular to the first leg 32, such the bent antenna 30 is L-shaped. The straight antenna 28 and the bent antenna 30 may be arranged such that the first leg 32 is substantially parallel to the straight antenna 28, and the second leg 34 extends from one end of the first leg 32 toward the straight antenna 28, being substantially perpendicular to both first leg 32 and the straight antenna 28. For the purposes of this disclosure, substantially perpendicular means that the second leg is perpendicular within a tolerance that retains the functionality of the plasmonic metasurface to produce evanescent IR light within 100 nanometers of the plasmonic metasurface. In one example, this tolerance may be ±45°. The plurality of antenna pairs may be arranged in a periodic formation (a pattern), such as a grid formation, shown in FIG. 4.

In the multicore embodiment, each metasurface 14 of each core 26 may resonate over the same range of infrared frequencies. In another embodiment, some of the plasmonic metasurfaces 14 of some of the cores may resonate at a frequency or range of frequencies that is different than the metasurfaces of other cores 26. Indeed, each core 26 may resonate at its own unique frequency. This may be beneficial to analyze multiple kinds of cell types or diagnose different kinds of cancerous cells using the same fiber 12.

Figure 5:
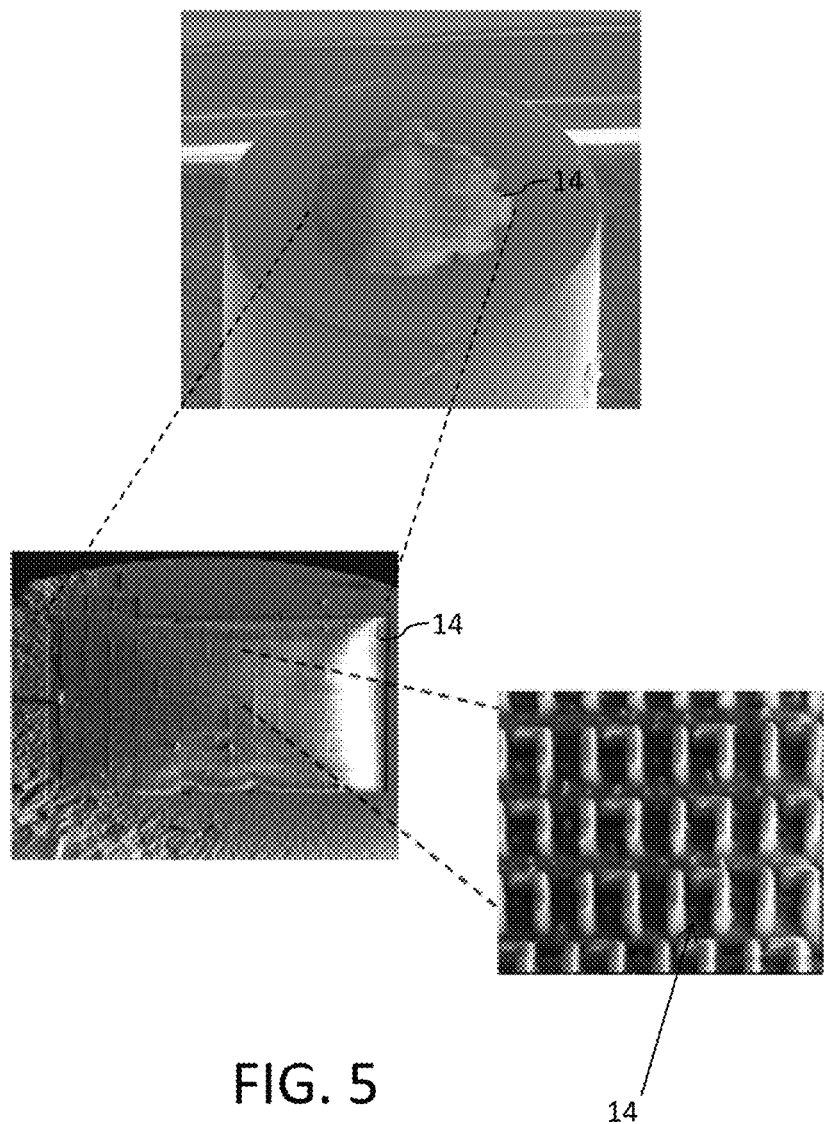
FIG. 5 depicts images of a plasmonic metasurface, according to an embodiment.

FIG. 5 depicts three images of the plasmonic metasurface 14 as deposited on a cleaved fiber 12 chalcogenide core. The images further depict the periodic formation of straight antennas 28 and bent antennas 30.

Although the straight antenna 28 and bent antenna 30 pair is depicted in the figures, one of ordinary skill in the art will appreciate, in conjunction with a review of this disclosure, that other kinds of plasmonic metasurfaces—providing the properties necessary to probe a cell membrane—may be used. For example, instead of each pair including one straight antenna and one bent antenna, each antenna pair may include two straight antennas. Alternately, instead of antennas, split rings or other geometries may be used, provided that the features necessary for analyzing cell membranes result.

As mentioned above, the plasmonic metasurface 14 is configured to yield strong localization of the evanescent optical fields in the immediate proximity of the plasmonic metasurface 14. Indeed, to properly probe the membrane portion of the cells under test, the evanescent IR light must be localized by the plasmonic metasurface 14 to sub-100 nanometer distances from the plasmonic metasurface 14. Failing to localize the evanescent IR light to within this range will result in penetrating a cell under test too deeply, thus failing to analyze the membrane of the cell.

Figure 6:
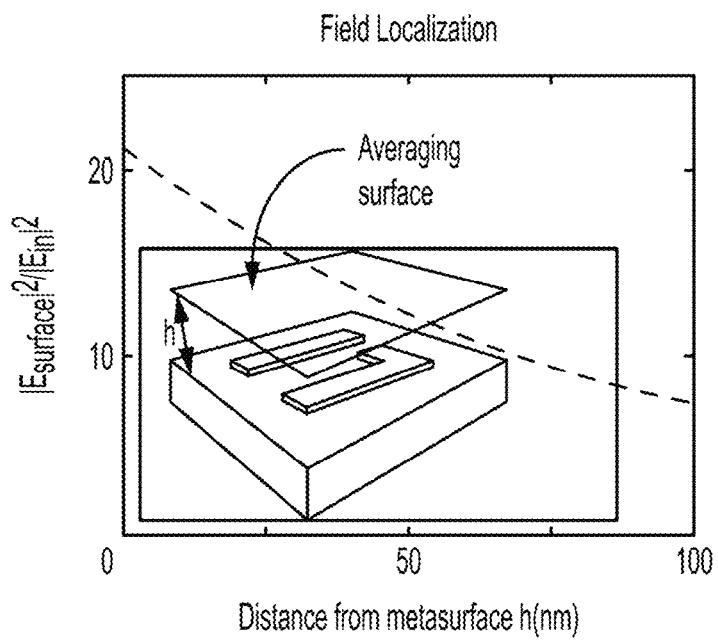
FIG. 6 is a graph of field localization provided by a plasmonic metasurface, according to an embodiment.

FIG. 6 is graph showing the localization of the evanescent field emitted by a metasurface 14, such as described in connection with FIGS. 2, 4, and 5, as function of distance from metasurface 14. More particularly, the strength of the evanescent field is depicted as averaged over averaging surface, shown inset in FIG. 6, over distance h from the metasurface 14 surface. As shown, evanescent field intensity drops by half over the distance of h=20 nm away from the metasurface.

Furthermore, the plasmonic metasurface is configured to provide enhancement within the evanescent field. For the purposes of this disclosure, enhancement is with respect to IR light emitted at the tip of an unpatterned IR fiber. Stated differently, the plasmonic metasurface 14, affixed to the tip of an IR transparent fiber 12, will localize and enhance the evanescent field as compared to the same IR transparent fiber 12 without the plasmonic metasurface 14, such that the membrane of a cell in contact with the metasurface 14 may be analyzed with reflective spectroscopy. Thus, the plasmonic metasurface 14 provides strong light concentration and localization in the evanescent or near-field region as compared to the IR light emitted by an unpatterned IR fiber. For example, as compared to unpatterned chalcogenide fibers (receiving mid-infrared light) or conventional silica fiber (receiving near-infrared light), the patterned end of the plasmonic metasurface 14 provides greatly enhanced near-field IR light. Indeed, the resonant nature of plasmonic metasurfaces provides stronger field enhancements than other methods of enhancing the localized IR light such as roughed-gold surface-enhanced infrared absorption spectroscopy (SEIRAS) substrates. Thus, the plasmonic metasurface is capable of strong light concentration and localization in the immediate proximity of the fiber tip (i.e., in the evanescent, or near-field, region).

Figure 7:
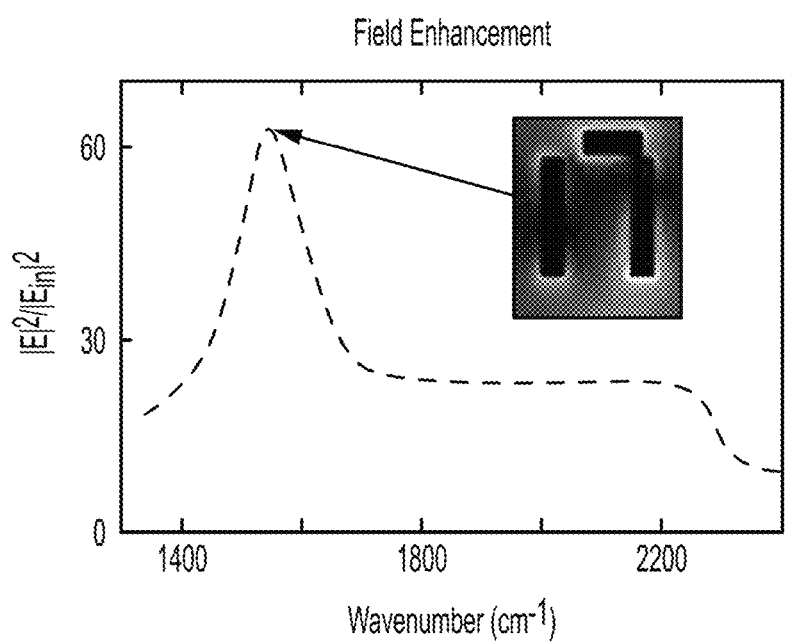
FIG. 7 is a graph of field enhancement provided by a plasmonic metasurface, according to an embodiment.

As shown in FIG. 7, the metasurface geometry of FIGS. 2, 4, and 5 is configured to provide a spectrally flat near-field intensity enhancement over a significant portion of the fingerprint region (e.g., ωv=900-1800 cm−1). Inset in FIG. 7 is a single antenna array pair showing field enhancement in the brighter regions.

One important drawback of unpatterned fiber evanescent wave spectroscopy (FEWS) is that the evanescent optical fields of a fiber penetrate the distance of order $\iota_d \sim \lambda/(2\pi)$, where λ is the wavelength of light. For λ≈6 μm (corresponding to the vibrational frequencies $\omega_{Amide} \sim 1600$ cm$^{-1}$ of the amides), $\iota_d \sim 1$ μm. Unfortunately, most of the changes between normal and neoplastic cells is expected to occur in or around the cellular membrane. The thickness of the cellular membrane in mammalian cells is only 5-10 nms, and the separation between cells and the sensing substrata is estimated to be from 10-15 nanometers (for focal contacts)

to 30-50 nanometers (for close contacts). Therefore, the large penetration depth of FEWS results in sampling the less relevant interior of the cell. Moreover, it is nearly impossible to sample a very small region of the tissue using FEWS because a significant segment of the fiber must be in contact with the analyzed tissue in order to conduct transmission experiments. This creates a potential toxicity issue of unprotected chalcogenide fibers. The approach of using near-infrared silica fiber red light enables much shorter penetration depth but cannot take advantage of vibrational spectroscopy because there are no clear molecular fingerprints at such short wavelengths. Thus, the plasmonic metasurface 14 tipped fiber 12, of the present disclosure, resolves the localization issues of competing approaches.

Figure 8:
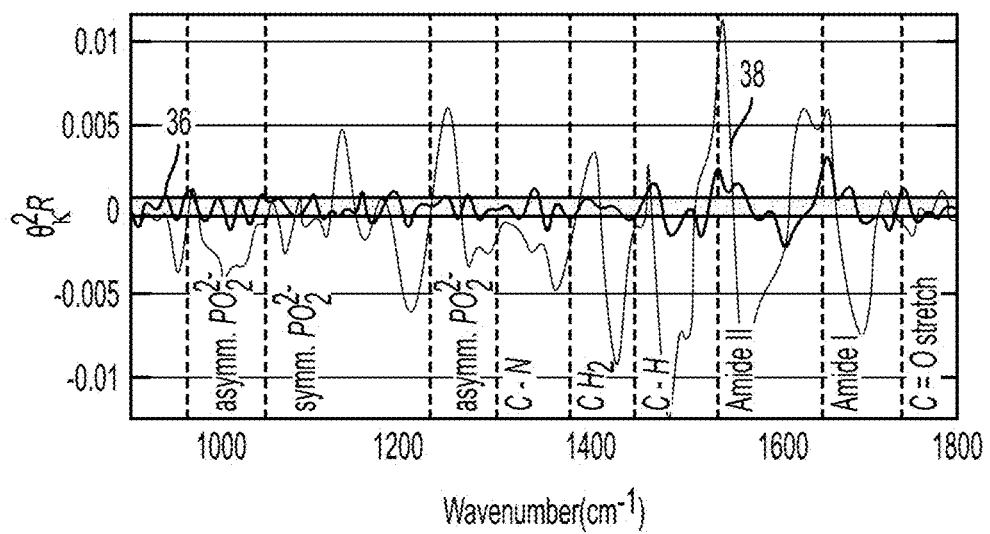
FIG. 8 is a graph of improved reflectively provided by a plasmonic metasurface, according to an embodiment.

In addition, in order to carry out mid-IR spectroscopy intra-operatively, it is necessary to carry out the spectroscopic characterization of the cells in reflection, rather than transmission. But reflection from a cell is low, due to the low refractive index contrast between the a typical fiber and tissue, as demonstrated by FIG. 8 (line 36) obtained by depositing the cells on a CaF2 substrate and then reflecting the light from the cell through the substrate. By contrast line 38 depicts the reflectivity of plasmonic metasurface 14. Thus, the plasmonic metasurface 14 provides the enhanced reflectivity (over, e.g., an unpatterned fiber) necessary to observe the vibrational features of the cell membrane and perform reflective spectroscopy.

Figure 9A:
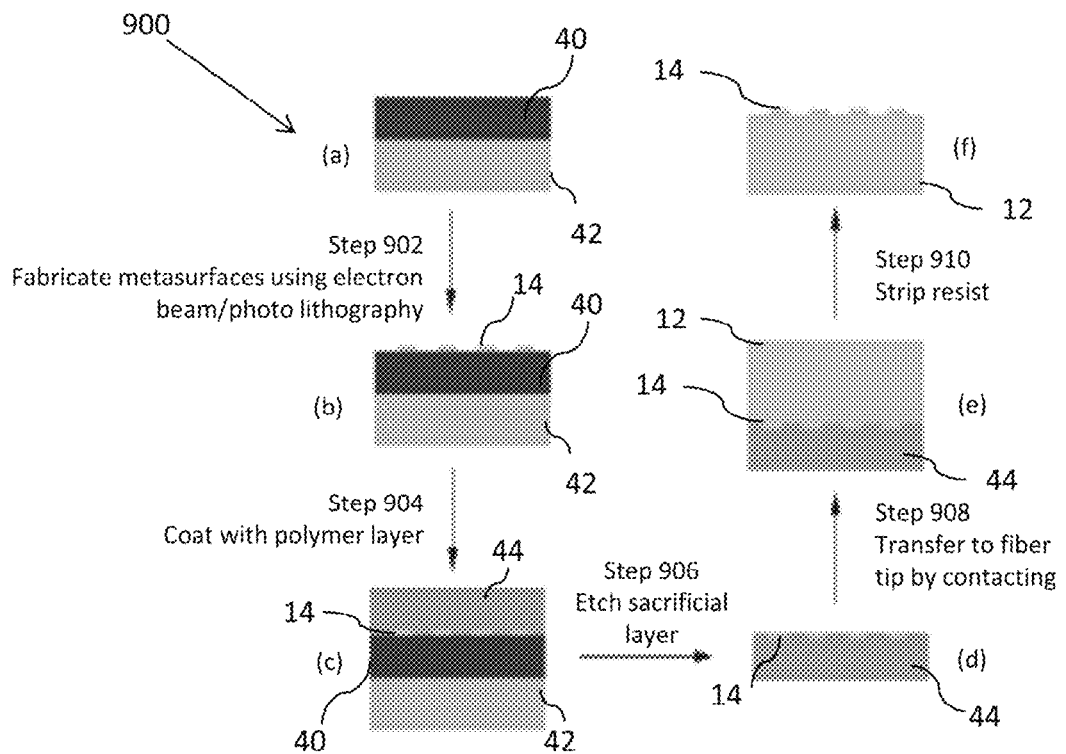
FIG. 9A is a method of depositing a plasmonic metasurface on a fiber tip, according to an embodiment.
Figure 9B:
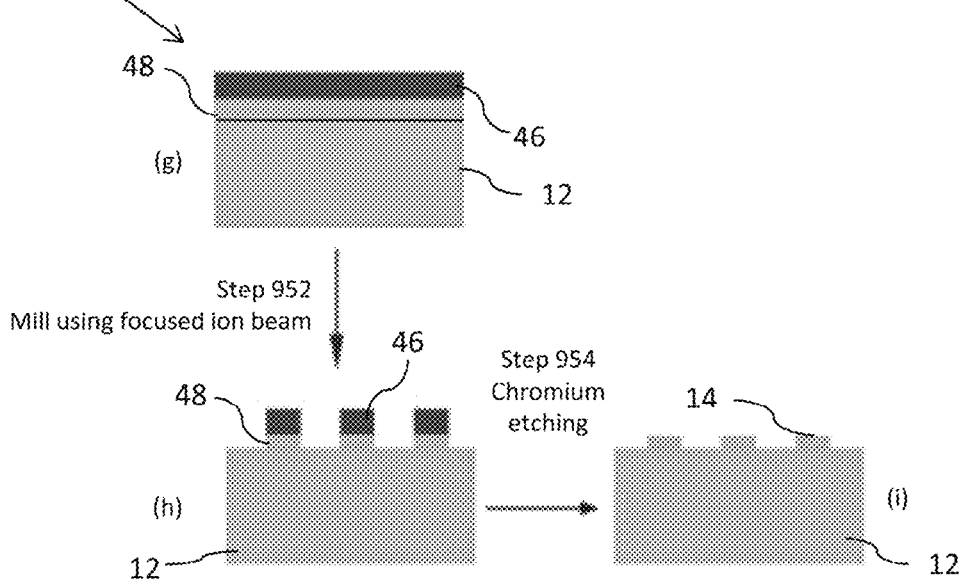
FIG. 9B is a method of depositing a plasmonic metasurface on a fiber tip, according to an embodiment.

FIGS. 9A and 9B depict two methods of depositing plasmonic metasurface 14 on the tip of fiber 12. In the method shown in FIG. 9A, the metasurface may be fabricated using electron beam lithography. Alternately, in the method shown in FIG. 9B, the plasmonic metasurface may be fabricated using focused ion beam milling.

Turning first to FIG. 9A, there is shown a method 900, together with the various accompanying stages of fabrication, represented as (a)-(f). Beginning with stage (a), sacrificial layer 40, comprising, for example copper or chromium, on a glass substrate 42 is provided. At step 902, metasurfaces are fabricated on the surface of sacrificial layer 40 using electron beam or photo lithography, yielding stage (b), comprising the plasmonic metasurface 14 disposed on top of the sacrificial layer 40 which is, in turn, on top of glass substrate 42. At step 904, the surface of sacrificial layer 40, including plasmonic metasurface 14, is coated with a polymer, such as PMMA. Step 904 yields stage (c) which comprises, from the top down, polymer layer 44, plasmonic metasurface 14, sacrificial layer 40, and glass substrate 42. Next, at step 906, the sacrificial layer 40 is etched away, yielding stage (d), which comprises the polymer layer 44 containing plasmonic metasurface 14. At step 908, the fiber 12 is brought into contact with surface of polymer layer 44 containing the plasmonic metasurface 14, transferring, by the contact, plasmonic metasurface 14 to the surface of fiber 12. At step 910, the polymer layer 44 is removed via a strip resist process, yielding the final stage (f), which is fiber 12 having the plasmonic metasurface 14 disposed on its surface.

In an alternative embodiment, instead of electron beam lithography, nanoimprint lithography may be employed. Nanoimprint lithography is an approach involving making a single hard mask, then using the mask to stamp the features into a soft polymer that is cured using UV light during the imprint. The nanoimprint lithography process provides a means for large-area replication of the device pattern after an initial electron beam lithographic process is used to generate the reticle.

Turning to FIG. 9B, there is shown the second method 950 for depositing plasmonic metasurface 14 on the tip of fiber 12, which uses focused ion beam milling, together with the accompanying stages of fabrication, represented as (g)-(i). Beginning with stage (g), protection layer 46, comprising, e.g., chromium, is disposed on a top of a gold layer 48, which, in turn, is disposed on top of fiber 12. At step 952, the chromium and gold is milled using a focused ion beam. At step 954, the protection layer is removed via chromium etching, to yield stage (i), which comprises plasmonic metasurface 14 deposited on tip of fiber 12. Because method 950 requires removing most of the metal of stage (g), this is the costlier of the two methods.

To prevent oxidation of fiber 12 and possible leakage of arsenate ions, appropriate fiber 12 encapsulation techniques that involve depositing thin dielectric layers on the tip of the fiber, as on its sides, may be employed. For example, a passivating and protective layer like silicon dioxide ($SiO_2$) or alumina ($Al_2O_3$) may be used. Note that, because most of the fiber typically comes coated with UV-cured plastic from the manufacturer, only the final 1-2 mm of the fiber need to be side-coated.

Figure 10A:
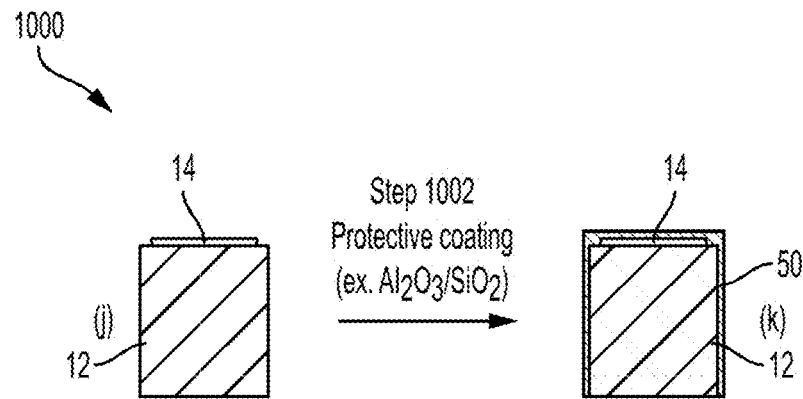
FIG. 10A is a method of encapsulating a fiber, according to an embodiment.
Figure 10B:
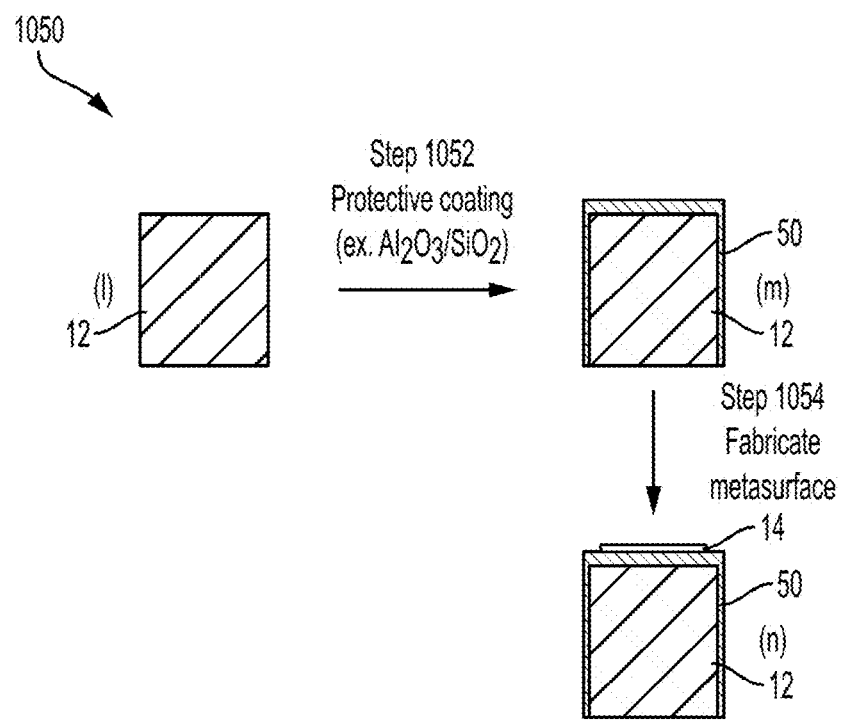
FIG. 10B is a method of encapsulating a fiber, according to an embodiment.

FIGS. 10A and 10B depict two of such methods to encapsulate fiber 12. Both of these methods use an electron beam evaporation technique for applying the protective coating. The thickness of the protective coating may be chosen to maximize biocompatibility.

FIG. 10A depicts method 1000 for encapsulating fiber 12. Method 1000 encapsulates metasurface in the protective coating. This increases the mechanical stability of the fiber 12 and metasurface 14, as well as the reusability of the fiber and biocompatibility (as the entire fiber 12 and metasurface 14 is coated). In method 1000, at stage (j), the fiber 12 is provided with metasurface 14 already deposited on top. At step 1002, the protective coating is applied to both fiber 12 and metasurface 14, yielding, at stage (k), fiber 12 and metasurface 14 both encapsulated in protective coating 50.

FIG. 10B depicts method 1050 for encapsulating fiber 12. In this method, only fiber 12 is encapsulated, with metasurface 14 being deposited on top of protective coating 50. This method yields increased sensitivity of the metasurface (because it is not coated with a protective coating), but still increase biocompatibility as compared to an encapsulated fiber 12. Method 1050 begins at stage (l) with fiber 12, which is encapsulated with protective coating 50 at step 1052, to yield stage (m). At step 1054, metasurface 14 is fabricated on top of encapsulated fiber 12 to yield stage (n). In alternate embodiments, instead of coating fiber 12 with passivating layers, fiber encapsulation will be based on an atomic layer deposition (ALD) method or plasma enhanced chemical vapor deposition (PECVD).

Figure 11:
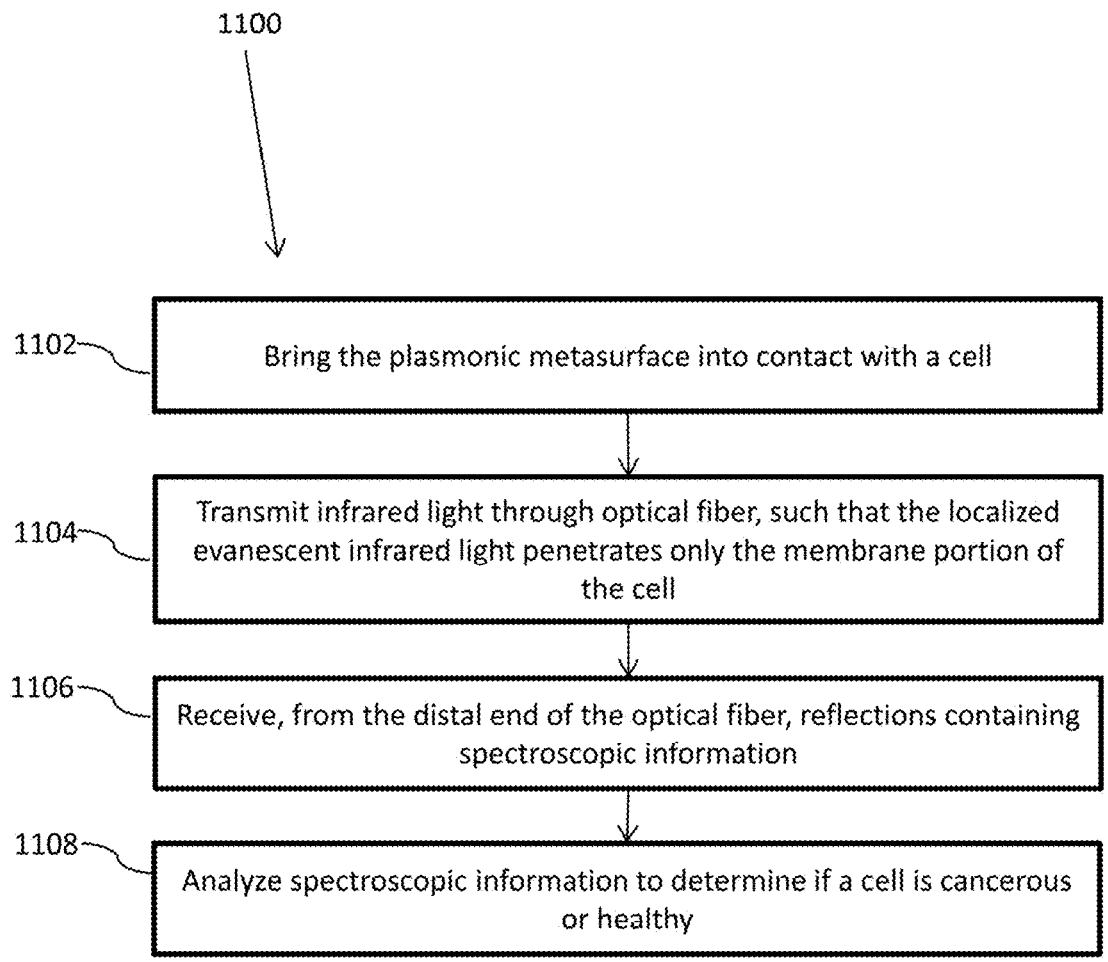
FIG. 11 is a flowchart of a method of performing reflective spectroscopy, according to an embodiment.

Turning to FIG. 11, there is shown a flowchart of a method 110 for using integrated device 10 for analyzing. In step 1102, plasmonic metasurface 14 is brought into contact with the tissue under test 18, which comprises at least one cell. Here, bringing the plasmonic metasurface into contact means bringing plasmonic metasurface near enough to the cell that the localized infrared light penetrates only the cell membrane. Typically, this will mean that the plasmonic metasurface 14 is in direct contact with the surface of the cell; however, in certain embodiments, plasmonic metasurface 14 may be encapsulated with a passivating or other coating, in which case the coating, rather than the plasmonic metasurface 14 itself will be in direct contact with the cell—it should be understood that, for the purposes of this disclosure, such intimate placement of the plasmonic metasurface 14 to the surface of the cell is deemed to be in contact with the cell.

At step 1104, IR light is received from a device such as spectrometer 16 and conducted through fiber 12 to the plasmonic metasurface 14. Such light may be modulated infrared light. As has been described in detail above, plasmonic metasurface 14 will begin to conduct localized infrared light within 100 nm of the plasmonic metasurface 14, and thus will only penetrate the membrane of the cell.

At step 1106, light reflected from the cell, containing spectroscopic information, will be returned through the distal end of fiber, back-propagated through fiber 12, to spectrometer 16 or other device.

At step 1108, the spectroscopic information is analyzed by spectrometer 16 (or other device) to determine if a cell is cancerous or noncancerous. Such analysis examines the spectroscopic information for vibrational fingerprints of different kinds of cells, such as normal or neoplastic cells. One such analysis technique is Principal Component Analysis (PCA). Additional analysis may be conducted to determine if the cell is precancerous, or what type of cancer the cell represents. It is also anticipated that other analysis may be conducted to determine other valuable information about the cell.

Method 1100 may be carried intraoperatively, by bringing the distal end of fiber 12 and plasmonic metasurface 14 into contact with in vivo tissue. For example, fiber 12 may form a movable probe to be inserted into a patient in order to map out tumor margins and to thus determine the exact portion of a neoplasm to remove. In such an example, it is essential that the tip of fiber 12 does not remove cells after being retracted from the tissue 18; otherwise, it will be impossible to spectroscopically interrogate any adjacent region of the tissue 18, because the tip will already be bio-fouled. Thus, in an embodiment, fiber 12 tip may be coated with non-toxic organic polymer coating, such as polyethylene glycol (PEG). Other suitable polymers may also be used.

Figure 12A:
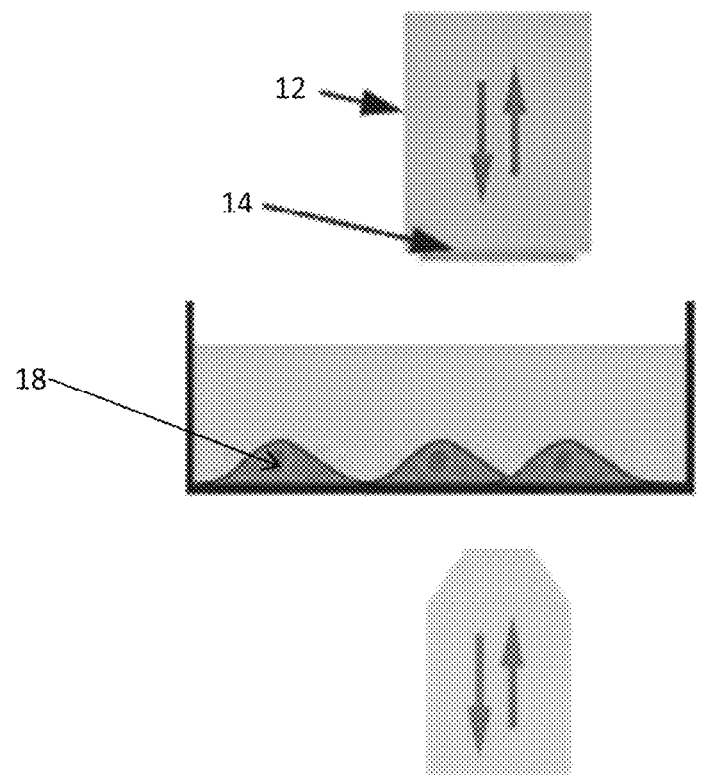
FIG. 12A is a block diagram of a fiber with a plasmonic tip held over a tissue sample, according to an embodiment.
Figure 12B:
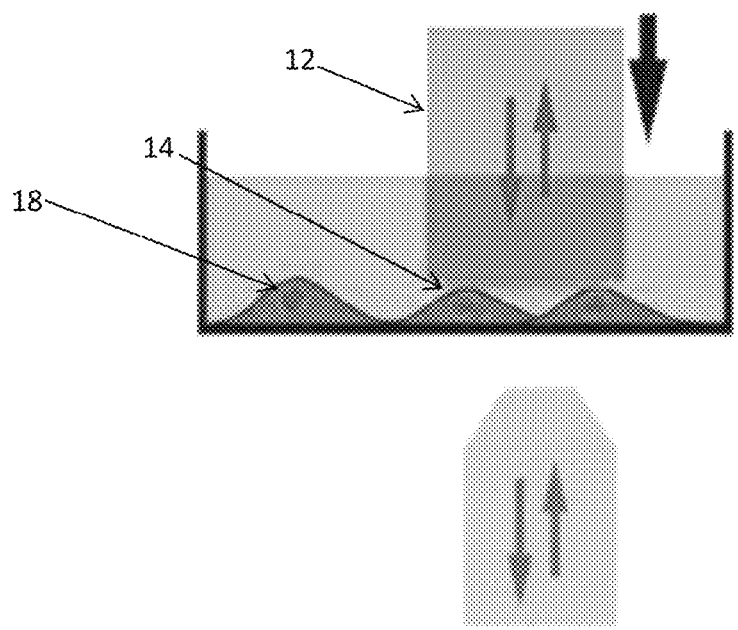
FIG. 12B is a block diagram of a fiber with a plasmonic tip in contact with a tissue sample, according to an embodiment.

Although in the above example, integrated device 10 is used for intraoperative in vivo reflective spectroscopy, it should be emphasized that integrated device 10 may be used for ex vivo and non-clinical applications as well. For example, as shown in FIGS. 12A and 12B, in one application, integrated device 10 may be used to analyze living cells (tissue 18) in a saline solution. FIG. 12A shows the integrated device in a retracted state, and FIG. 12B shows the fiber 12 in a contact mode for receiving IR signal from cells of tissue 18.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, and/or method described herein. In addition, any combination of two or more such features, systems, articles, materials, kits, and/or methods, if such features, systems, articles, materials, and/or methods are not mutually inconsistent, is included within the inventive scope of the present disclosure.

What is claimed is:

1. An integrated device for the detection of cancerous tissue, comprising:
   an optical fiber configured to receive at a first end modulated infrared light and to conduct the modulated infrared light from the first end to a second end; and
   a plasmonic metasurface, disposed on the second end of the optical fiber, configured to localize evanescent infrared light to sub-100 nanometer distances from the plasmonic metasurface of the optical fiber such that the localized evanescent infrared light penetrates only a membrane portion of a cell held against the second end, wherein the second end is configured to receive reflected light reflected from the membrane portion the cell, the reflected light including spectroscopic information indicative of whether the cell is noncancerous or cancerous.

2. The integrated device of claim 1, wherein the plasmonic metasurface is configured to enhance the strength of the localized evanescent infrared light.

3. The integrated device of claim 1, wherein the plasmonic metasurface is configured to enhance the reflection of the evanescent infrared light.

4. The integrated device of claim 1, wherein the plasmonic metasurface is tuned to resonate at a vibrational band indicative of one of a cellular trans-membrane protein or a phospholipid.

5. The integrated device of claim 1, wherein the plasmonic metasurface is includes a plurality of antenna pairs arranged in a periodic pattern.

6. The integrated device of claim 5, wherein each of the antenna pairs comprises a straight antenna and a bent antenna, the bent antenna including a first leg and a second leg, wherein the first leg is arranged substantially parallel to the straight antenna, and the second leg is arranged at one end of the first leg, extending toward the straight antenna and being substantially perpendicular to first leg and the straight antenna.

7. The integrated device of claim 1, wherein the optical fiber comprises a plurality of cores, each core including, at an end, a respective plasmonic metasurface.

8. A method for the detection of cancerous tissue, comprising the steps of:
   providing an optical fiber configured to conduct infrared light from a first end to a second end, and a plasmonic metasurface, disposed on the second end of the optical fiber, configured to localize evanescent infrared light to sub-100 nanometer distances from the plasmonic metasurface;
   bringing the plasmonic metasurface into contact with a cell;
   transmitting infrared light through the optical fiber, such that the localized evanescent infrared light penetrates only the membrane portion of the cell; and
   receiving from the second end reflected light reflected from only a membrane portion of the cell, the reflected light including spectroscopic information indicative of whether the cell is noncancerous or cancerous.

9. The method of claim 8, further comprising the step of analyzing the reflected light to determine if the cell is cancerous or noncancerous.

10. The method of claim 8, wherein the plasmonic metasurface is configured to enhance the strength of the localized evanescent infrared light.

11. The method of claim 8, wherein the plasmonic metasurface is configured to enhance the reflection of the evanescent infrared light.

12. The method of claim 8, wherein the plasmonic metasurface is tuned to resonate at a vibrational band indicative of one of a cellular trans-membrane protein or a phospholipid.

13. The method of claim 8, wherein the plasmonic metasurface is includes a plurality of antenna pairs arranged in a periodic pattern.

14. The method of claim 13, wherein each of the antenna pairs comprises a straight antenna and a bent antenna, the bent antenna including a first leg and a second leg, wherein the first leg is arranged substantially parallel to the straight antenna, and the second leg is arranged at one end of the first leg, extending toward the straight antenna and being substantially perpendicular to first leg and the straight antenna.

15. The method of claim 8, wherein the optical fiber comprises a plurality of cores, each core including, at an end, a respective plasmonic metasurface.

\* \* \* \* \*